(12) United States Patent
Henderson et al.

(10) Patent No.: US 6,980,922 B2
(45) Date of Patent: Dec. 27, 2005

(54) COMPUTER SIMULATION MODEL FOR DETERMINING DAMAGE TO THE HUMAN CENTRAL NERVOUS SYSTEM

(75) Inventors: Fraser C. Henderson, Upper Marlboro, MD (US); Kingsley Joel Berry, Flint, MI (US)

(73) Assignee: Computational Biodynamics, LLC, Virginia Beach, VA (US)

( * ) Notice: Subject to any disclaimer, the term of this patent is extended or adjusted under 35 U.S.C. 154(b) by 133 days.

(21) Appl. No.: 10/682,376

(22) Filed: Oct. 9, 2003

(65) Prior Publication Data

US 2005/0080591 A1 Apr. 14, 2005

(51) Int. Cl.⁷ .................. G01C 17/00; G01B 11/02; G06K 9/00
(52) U.S. Cl. .................. 702/152; 702/159; 382/131; 382/132
(58) Field of Search .................. 702/152, 150, 702/153, 155, 159, 167; 382/128, 131, 132, 130

(56) References Cited

U.S. PATENT DOCUMENTS 5,891,060 A * 4/1999 McGregor et al. .......... 600/595
6,161,080 A * 12/2000 Aouni-Ateshian et al. .... 703/11
2002/0061126 A1 * 5/2002 Gerard et al. ................ 382/128

OTHER PUBLICATIONS

Ichihara et al, "Mechanism of the spinal cord injury etc.", J. Neurosurg (Spine 3) 99:278–285 (2003).

* cited by examiner

Primary Examiner—John Barlow
Assistant Examiner—Meagan S Walling
(74) Attorney, Agent, or Firm—William H. Eilberg

(57) ABSTRACT

A computerized model simulates the human spinal cord and makes it possible to draw inferences about the probability of future injury or the likelihood that specific injuries occurred in the past. The spinal cord is modeled by a plurality of two-dimensional graphs formed of a large number of finite elements. The two-dimensional graphs are stacked in positions corresponding to the measured positions of the spinal cord at various vertebral levels of a patient. The stacked graphs yield a three-dimensional model, which may be compared with similar data taken from other patients. The model may include the simulation of stress, applied to all or part of the spinal cord, resulting in a perturbed three-dimensional model which may again be compared with similar data taken from patients having known injuries. The invention can therefore be used, among other things, to verify claims of spinal injury as a result of vehicular or sporting accidents.

22 Claims, 11 Drawing Sheets

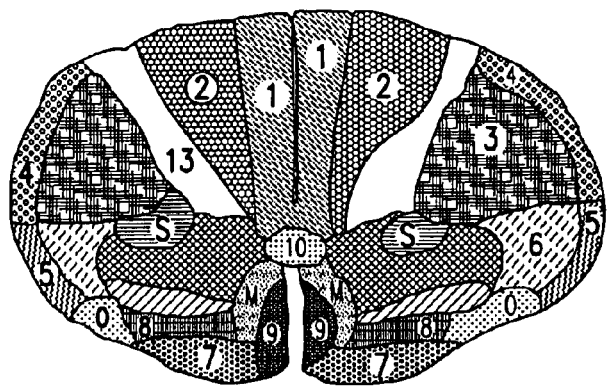

FIG.2A

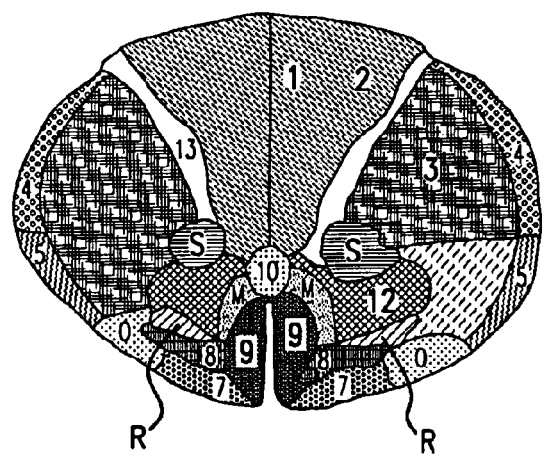

FIG.2B

1. FASCICULUS GRACILIS
2. FASCICULUS CUNEATUS
3. CORTICOSP + RUBROSP. TRACTS
4. DORSAL SPINO-CEREBELLAR
5. VENTRAL SPINO-CEREBELLAR
6. LAT. SPINOTHALAMIC TR.
7. ANT. SPINOTHAL TR.
8. TECTOSPINAL LATERAL + VESTIBULOSPINAL TRACTS
9. ANTERIOR CORTICOSP TR. RETICOLOSP.
10. ANTERIOR WHITE COMMISSURE
12. VENTRAL GRAY
M  MEDIAL LONGITUDINAL FASCICULUS
O  SPINO-OLIVARY TR.
R  RETICULOSPINAL FIBERS
S  INTERMEDIOLATERAL CELL COLUMN (DESCENDING AUTONOMIC FIBERS)

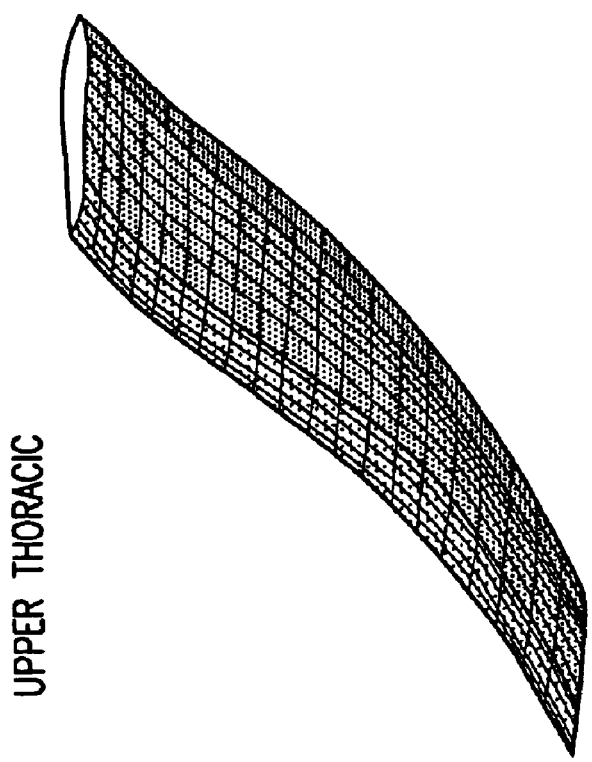
FIG.6D UPPER THORACIC
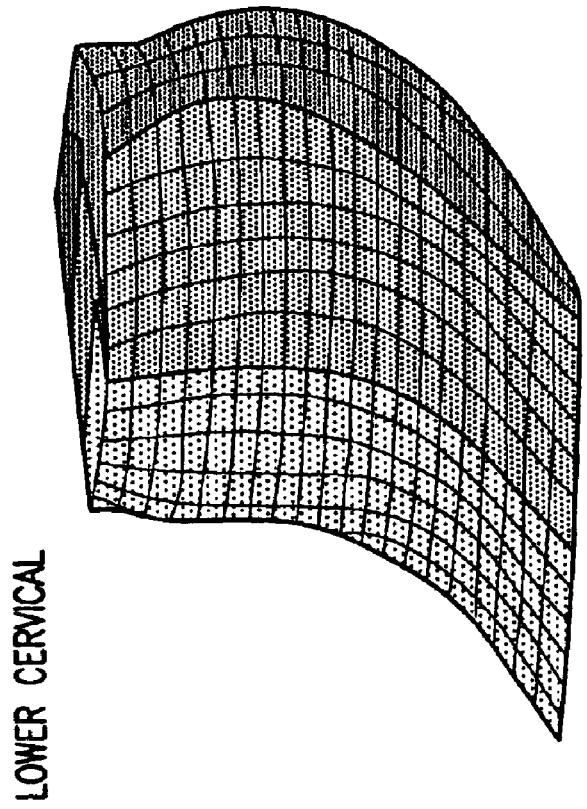
FIG.6C LOWER CERVICAL

CONTOUR FILL
sz
-1.0000E-02
-5.2632E-03
-5.2632E-04
4.2105E-03
8.9474E-03
1.3684E-02
1.8421E-02
2.3158E-02
2.7895E-02
3.2632E-02
3.7368E-02
4.2105E-02
4.6842E-02
5.1579E-02
5.6316E-02
6.1053E-02
6.5789E-02
7.0526E-02
7.5263E-02
8.0000E-02

MEDULLA 3 (svm)

MEDULLA 3 (sx)

MEDULLA 3 (sxz)

MEDULLA 3 (sz)

CONTOUR FILL
sz
-2.5000E-01
-5.2474E-01
-1.9947E-01
-1.7421E-01
-1.4895E-01
-1.2368E-01
-9.8421E-02
-7.3158E-02
-4.7895E-02
-2.2632E-02
2.6316E-03
2.7895E-02
5.3158E-02
7.8421E-02
1.0368E-01
1.2895E-01
1.5421E-01
1.7947E-01
2.0474E-01
2.3000E-01

MEDULLA 3 (svm)

MEDULLA 3 (sx)

MEDULLA 3 (sxy)

MEDULLA 3 (sz)

COMPUTER SIMULATION MODEL FOR DETERMINING DAMAGE TO THE HUMAN CENTRAL NERVOUS SYSTEM

BACKGROUND OF THE INVENTION

The present invention relates to the field of medical diagnosis, and provides a system and method for computerized modeling of the human spinal cord, for purposes of predicting the likelihood of spinal cord damage.

The invention provides a model of the central nervous system that is based on clinical data (e.g. neurological examination), circumstantial data (e.g., mechanism of injury, and injury-specific data, such as vehicle speed and angle of impact force vector with respect to the patient), and anatomical data (e.g., MRI, CT, Myelogram-CT, radiographs in flexion and extension, etc.). The invention produces a mathematical model that comprises a three-dimensional stress/strain image of the central nervous system. The model of the present invention also can provide a hypothesized finite element rendering of the central nervous system at the time of impact. The program can also predict the probability of neurological damage.

For many years, neurosurgeons, orthopedic spinal surgeons, and neuroscientists have grappled with the problems associated with spinal cord injury. Spinal cord injury is a major consequence of motor vehicle accidents, diving accidents, and sporting accidents. Well publicized examples of quadriplegia resulting from football accidents, for example, have drawn attention to the need for predicting when an individual is susceptible to, or at high risk for, a significant spinal cord injury.

Such predictions have been made, in the prior art, on the basis of static images derived from myelography, computerized tomography, and magnetic resonance imaging. Such imaging techniques, however, rely on interpretation of the anatomy of the patient in a neutral position, within the context of known standards, to make an assessment as to risk category. For instance, a football player with narrowing of the cervical spinal canal is considered at significantly greater risk than a football player with no narrowing of the spinal canal.

The presence of narrowing, in the above example, however, takes into account only the cross-sectional area of the spinal canal and the relative forces of compression placed on the spinal cord. Hitherto, neuroscientists and spine surgeons working with the spinal cord have placed excessive and perhaps undeserved importance on the presence of compression and consequent ischemia of the spinal cord. Proposed risk analysis strategies, therefore, have been suggested on the basis of compression and on the assumption that compression causes spinal cord injury via ischemia.

These assumptions, however, may be incorrect. New paradigms with animal models have demonstrated the importance of stretch and shear in neural injury. Other clinical studies suggest that spinal cord injury may largely be the result of the abnormal stretch and shear forces imparted to the spinal cord during excessive flexion, extension and lateral bending injuries. The importance of stretch and shear to chronic, non-traumatic injuries of the central nervous system seems pertinent.

While studies that model spinal stretch and shear can be performed in animals, they obviously cannot be demonstrated in humans. It is therefore desirable to develop a mathematical model of the spinal cord, and to apply an elemental analysis of the stresses applied, by an external load, to each biomechanically distinct region or tract of the spinal cord, and to measure the resulting strains. A computer simulation program can thus determine predicted loading patterns and stresses within the human spinal cord.

Spinal cord injuries often defy diagnosis. A patient may report symptoms such as pain, neurologic deficits, blurred vision, lack of hand coordination, change in gait, etc., yet the standard images formed by MRI scanners or the like may show nothing. The patient's strength and sensations may appear to be satisfactory, yet the patient is still suffering. The present invention is based, in part, on the hypothesis that many such injuries result from stretching or compression of the spinal cord, and that such stretching or compression is not readily observed by conventional means.

The present invention therefore provides a model of the spinal cord, and provides a method of simulating the loading patterns and strains within the spinal cord, so as to correlate certain patterns of strains with various kinds of central nervous system injury. The invention comprises, in part, a heuristic program which allows the model to develop information based on a database of accumulated clinical observations.

SUMMARY OF THE INVENTION

The present invention includes a method and apparatus for constructing a model of a human spinal cord. In a first embodiment of the method, one measures the positions of the spinal cord at a plurality of vertebral levels of a patient. The measurement can be done by X-rays, by CT scanning techniques, by magnetic resonance imaging (MRI), or by any other equivalent means. The information about the positions of the spinal cord at various vertebral levels are later used to construct a three-dimensional model of the spinal cord.

The three-dimensional model is assembled by combining a plurality of two-dimensional graphs, each of which represents a cross-section of the spinal cord of the patient at the location of each corresponding vertebra. Each two-dimensional graph is derived from a previously created model of the spinal cord at each respective location. The two-dimensional graphs are then stacked preferably by computer, so as to produce the three-dimensional model of all or part of the spinal cord. The two-dimensional graphs are preferably stored in a computer in digital form, to facilitate the assembly of the three-dimensional model by numerical means.

The three-dimensional model so obtained can then be stored in a database, and compared with data obtained from previous patients in a similar manner. Comparison of the data with data previously acquired, using a similar data acquisition technique, can be used to draw inferences about whether the patient has suffered, or is likely to suffer, a particular kind of spinal injury.

In another embodiment, the initial measurements are made while the patient assumes each of a plurality of positions. For example, measurements are taken when the patient is sitting in a "neutral" position, and when the patient is bending the head forward, as well as when the patient is bending the head backward. Three-dimensional models of the spinal cord can be generated for all of these cases, and the data compared with similar data taken from previous patients.

In still another embodiment, one simulates the application of stress to at least one portion of the spinal cord. The simulation can be made using a knowledge of the elastic properties of the material forming the spinal cord. The three-dimensional model produced by this embodiment still represents the spinal cord of a particular patient, because it is based on actual measurements of positions of the spinal cord at various vertebral levels, but it also includes the effect of the applied stress. By comparing this perturbed model of the spinal cord with data taken from previous patients, one can draw inferences about the nature of the injury suffered by the present patient. An important application of this embodiment is in verifying the accuracy of the testimony of a patient who claims to have suffered injury in an automobile accident or other accident.

The above-described method is preferably performed on an apparatus which provides a representation of the initial data taken from the patient, and which gives the operator the chance to select one or more points, from the images relating to the patient, for use in constructing the model. The apparatus then generates the three-dimensional models of the spinal cord, and gives the operator the option of adding constraints to simulate stresses. The apparatus can be programmed to provide a visual representation of the probabilities of various injuries to the patient.

The present invention therefore has the primary object of providing a method and apparatus for constructing a model of the spinal cord.

The invention has the further object of providing a method that enables a physician to predict the likelihood that a patient will suffer a particular kind of spinal injury.

The invention has the further object of providing a method that enables a physician to determine the probability that a patient has suffered a particular kind of spinal injury.

The invention has the further object of providing a technique for evaluating the accuracy of claims of spinal injury.

The invention has the further object of applying finite element analysis to the field of neuroscience, so as to provide a predictive model of the spinal cord.

The invention has the further object of providing a mathematical model of the spinal cord which comprises a heuristic program, the usefulness of which is enhanced as more and more data are collected from more and more patients.

The reader skilled in the art will recognize other objects and advantages of the present invention, from a reading of the following brief description of the drawings, the detailed description of the invention, and the appended claims.

BRIEF DESCRIPTION OF THE DRAWINGS

FIGS. 2A and 2B are diagrams of cross-sections of the spinal cord at two vertical positions, corresponding to the C7 and T1 vertebrae, respectively, these cross-sections comprising functional models of the spinal cord used in constructing the three-dimensional finite-element model of the present invention.

FIGS. 6A–6D provide diagrams showing three-dimensional models of portions of the spinal cord, constructed by stacking two-dimensional models of the type illustrated by FIG. 5, according to the present invention.

DETAILED DESCRIPTION OF THE INVENTION

The present invention comprises a computerized model of the human spinal cord, the model being useful in determining the probability of various types of future injuries to the spinal cord, and in drawing inferences about how the spinal cord may have been injured in the past.

The present invention is predicated on the fact that the brain and spinal cord undergo stretching and deformation when subjected to stress. Such stresses may include flexion and extension, lateral bending, stretching, rotation, and compression of the spine or skull. The central nervous system (i.e. the brain and spinal cord) can return to its original position when subjected to normal loads. However, excessive stresses, due to lordosis or kyphosis, may induce excessive stretching of the spinal cord and brainstem, and excessive or abrupt rotation or translation may impart excessive shear forces to the brain and spinal cord. The presence of protuberances anywhere within the path of the brain, brainstem or spinal cord may also result in acute focal changes in load and deformation, and result in brain or spinal cord injury.

For purposes of illustration, the present invention will be described with respect to the lower skull and the cervical and upper thoracic spine. However, the principles of the invention can be applied to the brain and lower spinal cord as well as to the peripheral nerves. The examples given in this description deal specifically with the brainstem from the mid-medulla oblongata to the spinal cord at the mid-thoracic level.

Figures 1A, 1B:
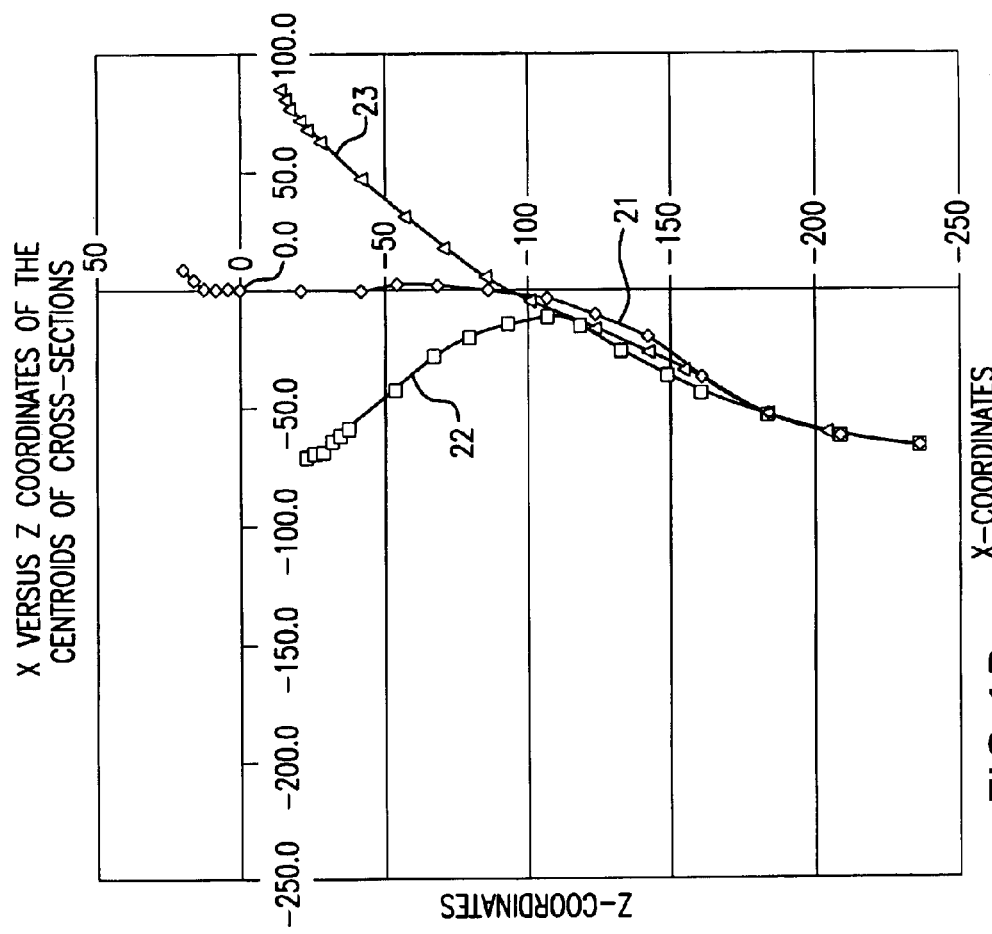
FIG. 1A is a diagram representing the orientation of the spinal cord of a patient in a resting, sitting position, wherein the position of the spinal cord is to be measured according to the present invention.
FIG. 1B is a graph showing the positions of portions of a patient's spinal cord, corresponding to various vertebral levels, the measurements being taken while the patient assumes various positions, according to the present invention.

The method of the present invention combines the gathering of clinical data with a mathematical representation of the spinal cord, such that a model can be derived that realistically represents the condition of a given patient. FIGS. 1A and 1B represent the step of gathering the clinical data.

FIG. 1A represents the spinal cord of a patient from whom data will be taken. The patient sits in front of a scanning device (not shown), which can be an X-ray machine, a CT-scanner, an MRI scanner, or any equivalent device that is capable of forming images of the vertebrae and/or spinal cord of the patient. The preferred device is an MRI scanner. The scanning device obtains data represented by the graphs of FIG. 1B.

In FIG. 1B, there are three curves, representing the spinal cord of the patient in three different positions. Curve 21 represents the neutral position, taken when the patient is sitting in a normal position. The finite symbols disposed along the curve correspond to positions of the spinal cord at various vertebral levels. The exact location of each such position is determined from the output of the scanning device. Curves 22 and 23 represent the spinal cord when the patient is bending the head backward and forward, respectively. The condition of bending the head forward is known as flexion, and the condition of bending the head backward is known as extension.

In each case, the scanning device records the position in space of the centroid of the spinal cord at each vertebral level, and stores the coordinates of each such centroid digitally for later use in assembling a model.

In practice, the movements of the cervical spine are extremely complex, and such movements may also include elongation of the spinal cord in an upward direction, and compression of the spinal cord in a downward direction. The spinal cord may also be subject to lateral bending and rotation. The data on the location of the centroid of the spinal cord at each vertebral level may be combined with data concerning the angle of inclination of the spinal cord around the x, y, or z axis. The data may also include an amount of impression or compression, to record the presence of any areas of stenosis (narrowing of the spinal canal). The more types of data that are used, the more precise the model can become.

So far, the procedure of the present invention has produced only information about the location of the centroid of the spinal cord at each vertebral level, while the patient is in one or more positions. To create a usable model of the spinal cord, there is needed more information about the structure of the cord at the locations corresponding to each vertebra.

The method of the present invention therefore also includes the development of two-dimensional models of the spinal cord, at each vertebral position, and, in the case of the brainstem, at every 4 millimeters length within the medulla oblongata. Two such two-dimensional models, pertaining to vertebral levels C7 and T1, are illustrated in FIGS. 2A and 2B. (Vertebrae are commonly identified by their locations; the seven cervical vertebrae are denoted C1 through C7 and the 12 thoracic vertebrae are known as T1 through T12. Locations in the medulla are denoted by M1 through M5.)

FIGS. 2A and 2B include a legend which identifies the various structures or regions of the spinal cord, as identified by the indicated numbers or letters.

The two-dimensional cross-sectional models represented in FIGS. 2A and 2B are believed to describe the full scope of spinal cord structure and neurological function at each level. These two-dimensional models are based on knowledge of the anatomy of the spinal cord, and on the latest experimental work and theory about the function of each portion of the spinal cord. In some cases, the location of certain structures is not clearly defined in the human body. For example, the location of the fibers of the sympathetic outflow system (the intermedio-lateral cell column). in the cervical spinal cord, is not clearly known, although these fibers are known to be very important for regulating blood flow, body temperature, flow of air through the lungs, movement of food through the gastrointestinal system, and sexual and genito-urinary function. In such cases. assumptions are made as to the locations of these fibers within the spinal cord. Similarly, the neurological apparatus for regulation of breathing are poorly understood. In generating a model of the spinal cord it is useful to group certain brainstem nuclei with similar neurological functions, and to ascribe to them a common material property in order to make basic assumptions as to the effect of stretch and load on certain neurological functions.

The models represented in FIGS. 2A and 2B therefore divide the two-dimensional cross-sections of the spinal cord into regions, each region being associated with a particular neurological function. As knowledge of the spinal cord progresses, these models can be modified to reflect better understanding that may be obtained in the future. Thus, although the specific content of these two-dimensional anatomical models might change, the underlying methodology of the present invention would remain substantially unchanged.

From the two-dimensional anatomical models developed for each level of the central nervous system, as illustrated in FIGS. 2A and 2B there are derived digital representations in the form of two-dimensional graphs, that can be conveniently stored in a computer and numerically manipulated. The first step in this procedure is illustrated in FIG. 3.

Figure 3:
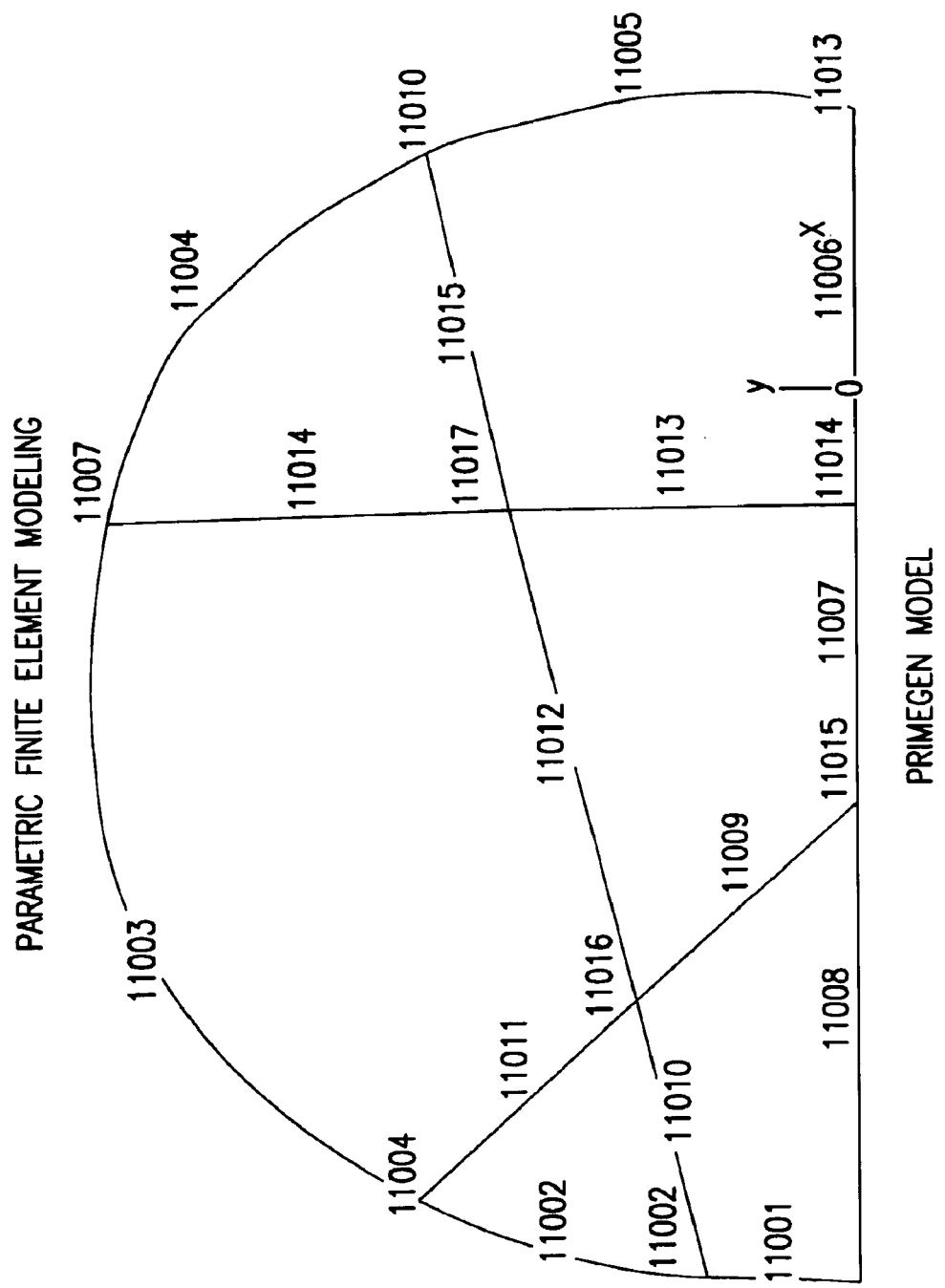
FIG. 3 is a diagram of a cross-section of a portion of the spinal cord of the patient, the diagram showing the division of the cross-section into regions, using the model of the present invention.

FIG. 3 represents a cross-section of the spinal cord at a given location, and corresponds generally to the cross-sectional diagrams shown in FIGS. 2A and 2B. The cross-section shown in FIG. 3, however, is greatly simplified. FIG. 3 shows a generally semicircular region that is divided into subregions by straight lines which extend between points on the boundary of the region. These straight lines define boundaries of regions of the spinal cord, such regions being intended to correspond to distinct neurological functions. The boundary curve and straight lines of FIG. 3 are clearly simplified, and are presented in the illustrated form so that they can be readily digitized and stored in a computer memory.

Figure 4:
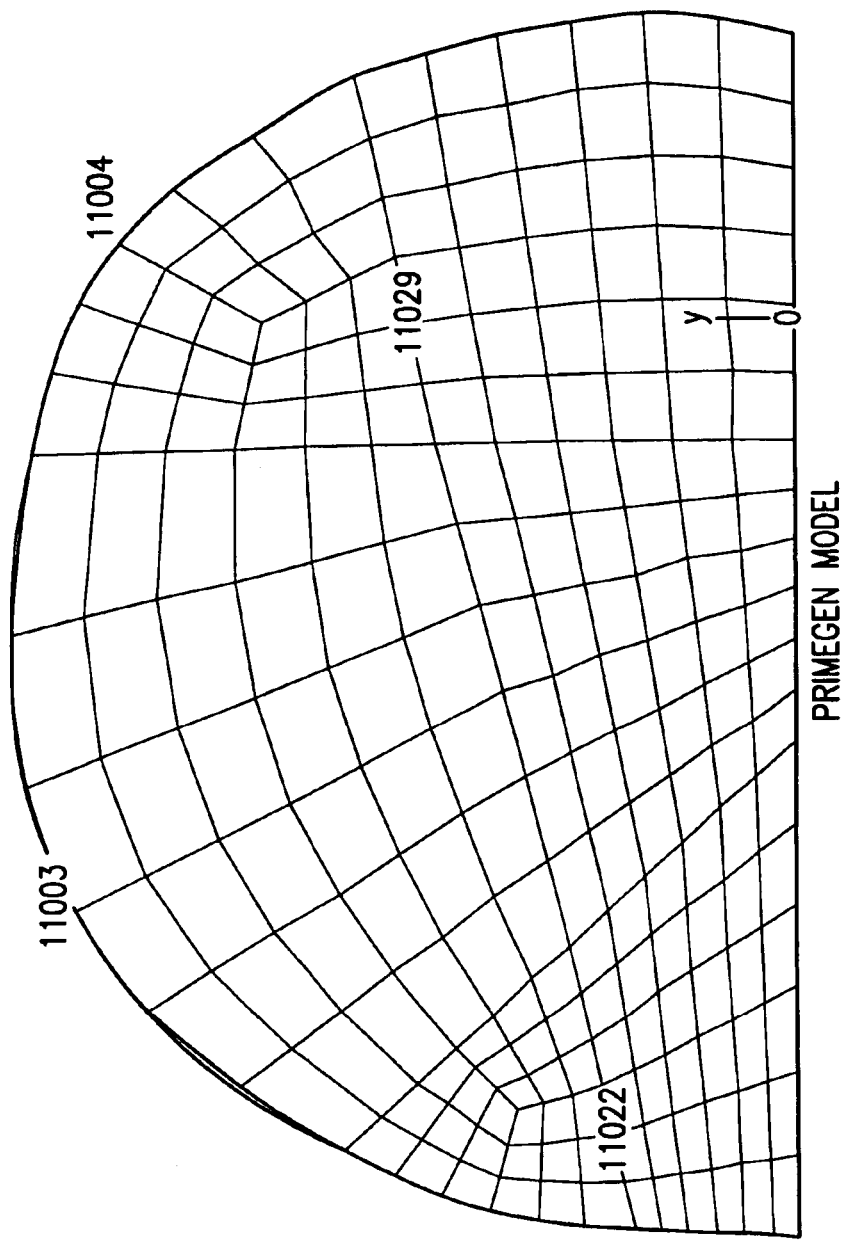
FIG. 4 is a diagram similar to that of FIG. 3, but with the addition of a plurality of finite element regions, enabling the cross section to be modeled and stored in a computer memory, according to the present invention.

FIGS. 3–9 may be developed with the aid of the computer program known as PRIME, which is commercially available from Geometrics, Inc. of Flint. Mich. The PRIME program is a microcomputer-based interactive graphics program which generates the finite element models used in the present invention, and which enables interpretation of the subsequent results of analysis. The program therefore facilitates the manipulation of data generated for each patient. The invention is not limited to the use of this particular program, however. The five-digit numbers shown in FIG. 3 and 4 represent hypothetical nodes stored by the PRIME program.

FIG. 4 represents the next step in the process. FIG. 4 is similar to FIG. 3, except that each region, as defined by the straight lines shown in FIG. 3, have now been subdivided into smaller regions. Thus, FIG. 4 shows that the cross-section of the spinal cord has been represented in terms of a large number of finite element subregions. In practice, the number of such subregions can become very large, if one decreases the average mesh size. The smaller the mesh size the greater the precision of the model. Each subregion is defined by vertices or nodes shown in the figure, and the coordinates of the vertices can be stored in digital form for later numerical processing.

Figure 5:
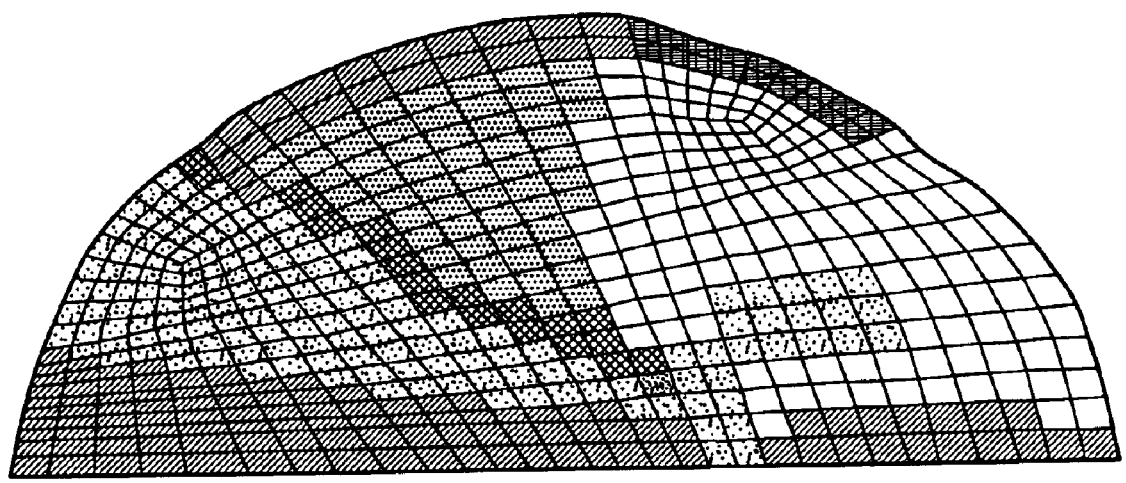
FIG. 5 is a diagram similar to that of FIGS. 3 and 4, wherein different finite element regions have been assigned different indicia to illustrate their respective functions.

FIG. 5 shows the next step in the process. In FIG. 5, the various finite subregions have been assigned indicia, which could be codes, patterns, colors, or their equivalent. Groups of such subregions, of a given color or pattern, represent areas of the spinal cord associated with the same neurological function. The representation of FIG. 5 therefore provides a visual depiction of the model of the cross-section of the spinal cord while still facilitating the storage of the data in digital form.

The next step in the process is the construction of three-dimensional models. A three-dimensional model is made by stacking a plurality of two-dimensional graphs of the type shown in FIG. 5. This stacking is preferably performed electronically by a computer. Each element in the stack must be positioned such that the centroid of the cross-section corresponds to the vertebral position measured by the scanning device. In this way, the model is specifically tailored to the patient being observed.

Figure 6B:
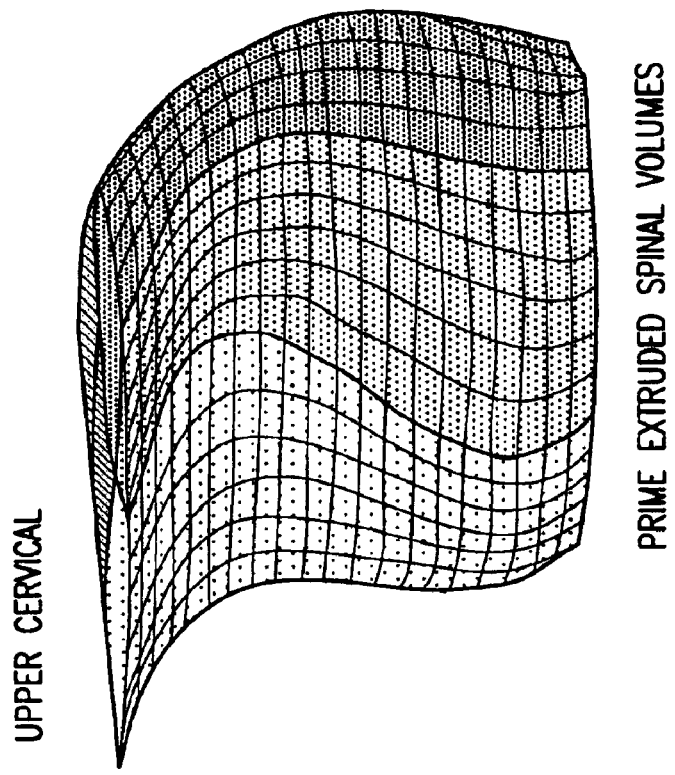
Figure 6A:
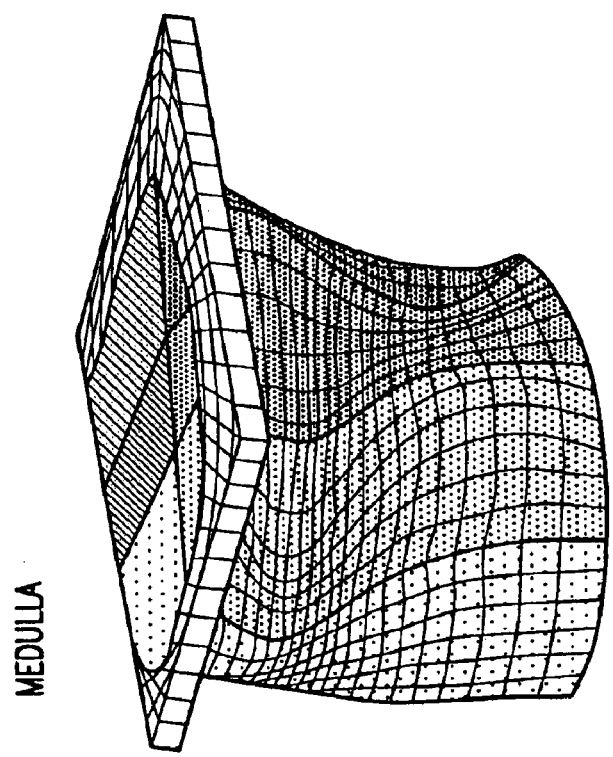
Figure 7D:
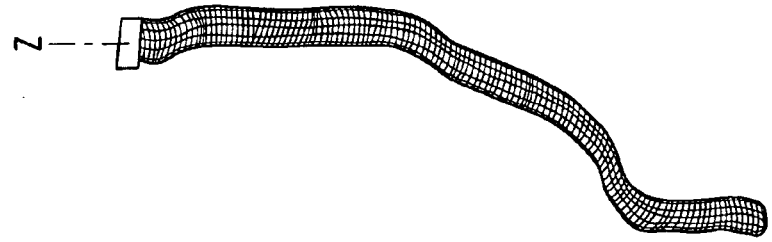
FIGS. 7A–7D provide diagrams showing three-dimensional models of the spinal cord, in various positions, constructed according to the present invention.
Figure 7C:
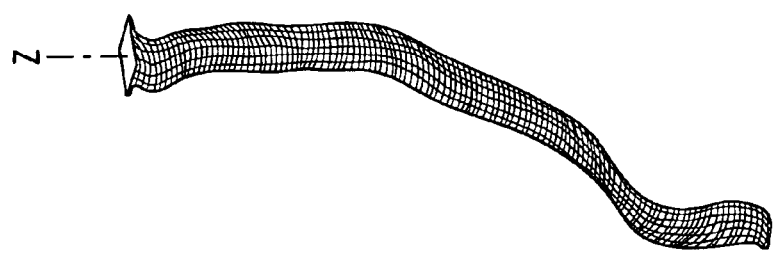
Figure 7B:
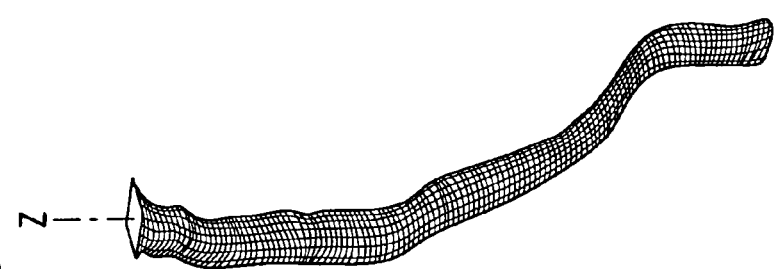
Figure 7A:
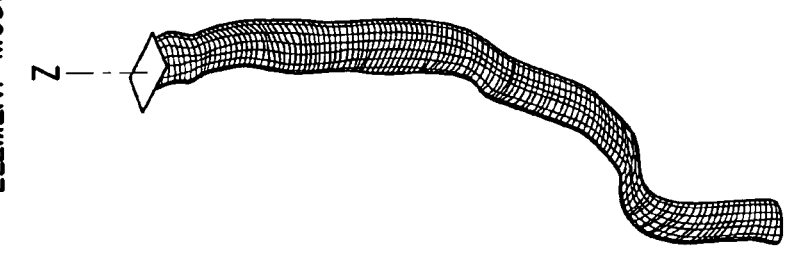

Sample results are shown in FIGS. 6A–6D. FIG. 6A represents a sample three-dimensional model of the medulla. FIGS. 6B–6D represent cervical-top, cervical-bottom, and thoracic-top models, respectively. These models can be viewed on a computer display, using commercially available software, or can be printed on paper as shown in the figures.

The three-dimensional models shown in FIGS. 6A–6D are representations of small portions of the spinal cord. Models of the full spinal cord can be generated in the same way simply by stacking a plurality of cross-sections of the spinal cord, taken at positions along the entire vertical length of the spine. FIGS. 7A–7D provide examples of models of the full spinal cord, showing the cord in four different positions.

In all of the examples given in FIGS. 6A–6D and 7A–7D, the models shown are constructed of a large number of finite elements, ultimately deriving from the finite elements used to model each cross-section, as shown in FIG. 4.

It can now be seen that the models of the spinal cord, shown in FIGS. 6A–6D and 7A–7D are based both on specific data derived from a patient and on a more general anatomical model of the structure of various cross-sections of the spinal cord. The method of the present invention makes the assumption that, for a variety of patients, the structure and size of each cross-section of the spinal cord is generally the same. The present invention therefore builds a model by assembling a plurality of two-dimensional models of portions of the spinal cord, each two-dimensional model being positioned to coincide with the measured location of the corresponding vertebra. Thus, although it is built with a model of general applicability, each three-dimensional model is unique to the patient being examined.

The models derived as described above can be used in different ways. A primary use is to compare a given model with data acquired from previous patients with known conditions. In the simplest case, the data could be stored for the neutral position only. That is, a database can be developed containing spinal models of a plurality of patients each model being obtained from data taken from patients sitting in the neutral position. If the condition of each patient in the database is known, new incoming data can be compared with the stored information to draw inferences about the current patient. For example, one might predict whether the current patient may be susceptible to a particular kind of spinal cord injury, based on similarities between the model of that patient's spinal cord and models of other patients suffering from known conditions. Or one might be able to verify a claim of injury, based on how closely a given patient's spinal cord resembles those of others who are known to have suffered similar injuries.

The comparison discussed herein can be done manually, such as by observing the model generated for a given patient, and comparing it subjectively with models stored from data acquired from other patients. Alternatively, the comparison could be automated, using a programmed computer to search for features that are shared by the given model and any one of the models stored in the database. The automated comparison could include a "brute force" calculation that simply computes a least-squares fit, or other fit, between the given model and the models in the database, or it could be a more sophisticated program that searches for subtle features that may be shared by the models being compared. The present invention is intended to include all such methods of comparison.

In the examples given above, the comparison is made solely with data taken in the neutral position. The method becomes more accurate when one uses data taken in a plurality of positions, such as those illustrated in FIG. 1B. The method that relies on multiple positions is essentially similar to the method that relies on only one position, except that more comparisons could be made between the data taken from the current patient and the data stored from other patients. In particular, it is possible to compare the given patient's spinal cord, in each of several different positions, with corresponding positions of the spinal cords of other patients.

Another important embodiment of the invention includes the simulation of stress applied to the spinal cord. Using a knowledge of the elastic properties of the materials constituting the spinal cord, one can simulate the movements of portions of the spinal cord in response to various stresses. The material properties of the spinal cord can be derived from an analysis of spinal cord tissue harvested from human cadavers. These material properties can be used to make realistic assumptions about how the spinal cord is affected by various stresses.

Thus, one begins with a model constructed as described previously. One then stresses the model in a known way, thereby deriving a model of the spinal cord in a perturbed condition. In theory, one can simulate the application of stress to the entire spinal cord, or to portions thereof, and one can stress different portions in different ways. The perturbed model has the same structure as described above. That is, the final model comprises a plurality of stacked cross-sections, each cross-section being a two-dimensional slice of the spinal cord, as represented by a plurality of finite elements. The advantage of the use of finite elements is especially evident here, as it is theoretically possible to simulate the application of a different kind of stress to each finite element.

Since the simulated stresses result in models which are represented using the same kind of data structures used in the static models described above, it is easy to compare the stressed models directly with spinal models taken from previous patients. The comparison can be made, as described above, either manually, by visually and subjectively comparing a given model with models taken from a database, or by automated means. The procedure of comparing a stressed model with models taken from a database is especially useful, for example, in determining the likely extent of spinal injury in an automobile accident, wherein the spinal cord is known to have been stressed for an instant at the time of the accident. One could also experiment by applying a series of different simulated stresses to the model, comparing each result with actual data. By doing so one can draw inferences as to whether and how a given patient was injured. One can also draw inferences as to the exact nature and extent of the load that was applied to a given patient's spinal cord during an accident.

FIGS. 8a–8d provide depictions of models of a stressed spinal cord at location M3, in the medulla, and FIGS. 9a–9d provide comparable depictions for location C5, in the cervical spinal cord.

Figure 8A:
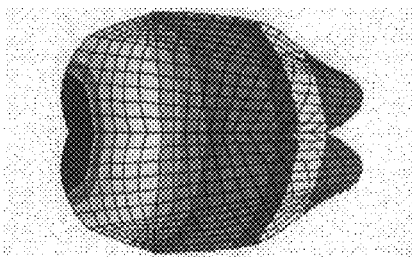
FIGS. 8a–8d provide diagrams of a perturbed portion of the lower brainstem (medulla), at location M3 constructed according to the present invention.
Figure 8B:
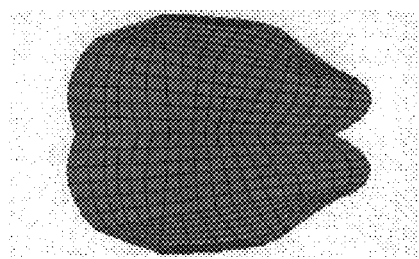
Figure 8C:
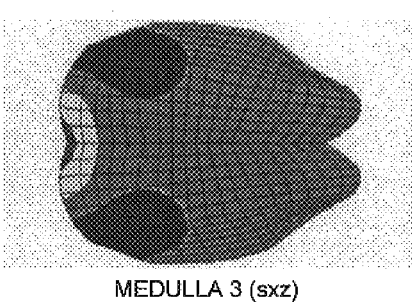
Figure 8D:
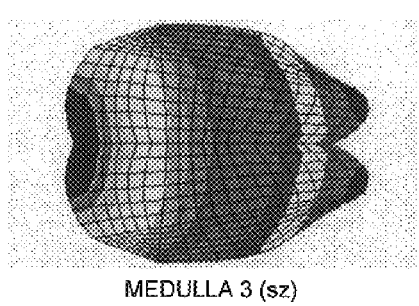
Figure 9A:
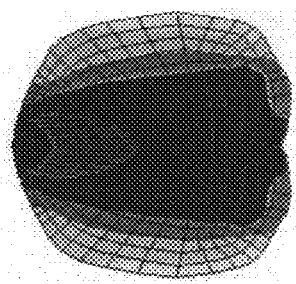
FIGS. 9a–9d provide diagrams similar to FIGS. 8a–8d, but pertaining to the spinal cord at vertebral location C5, i.e. the fifth cervical vertebrae.
Figure 9B:
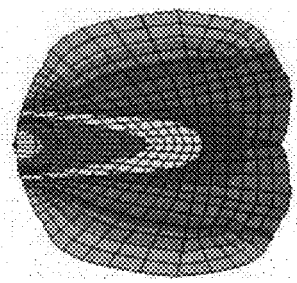
Figure 9C:
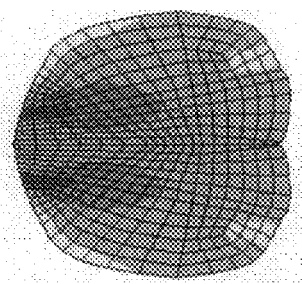
Figure 9D:
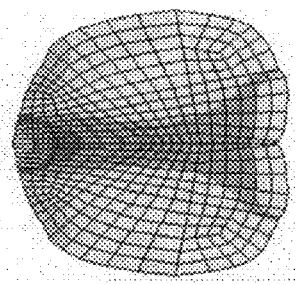

FIGS. 8a–8d represent the M3 cross-section for a 20 mm axial stretch and a 4 mm "pinch" applied between spinal locations C3 and C4. The results are provided for four stress components, namely axial stress (SZ) (FIG. 8d), lateral stress (SX) (FIG. 8b), axial-lateral shear (SXZ) (FIG. 8c), and Von Mises combined stress (SVM) (FIG. 8a). There are nine possible stress components and three possible deformation components. In FIGS. 8a–8d and 9a–9d, hypothetical stress components are depicted by the column of numbers on the left-hand side. Each such number is associated with a color or pattern code which corresponds to a similar code in the model of the spinal cord section. Thus, even by visual inspection of the model, one can clearly view the stresses applied.

One can make assumptions about the stresses applied to the spinal cord by studying actual patient injury data. Stresses will vary in their nature and intensity. On the one hand, one might model a stress that caused a football injury, representing severe nervous system damage, or a chronic stress applied to the spinal cord in the condition of spinal stenosis, representing a more mild, chronic injury.

The comparison between data obtained for a patient, and data stored in a database, can be made as follows. The database preferably includes stress/strain, stress/strain energy, and displacement results for each spinal cross-section (i.e. M1, M2 . . . C1, C2, etc.). For each cross-section, and for each element within each cross-section, the stress/strain data at each vertex or node of the finite element model is stored along with the deformed and undeformed coordinates of the vertex. The database may have hundreds or thousands of case files, wherein each case file contains the stress results along with an overall damage assessment based upon clinical observation. To compare each stored cross-section with the data obtained for the patient being examined, one can compare the strain energy at each vertex, and locate the case in the database showing the smallest cumulative difference from the data for the patient under examination. From this comparison, one can determine a match probability for each case in the database, and thus a prediction of the type of damage sustained by the patient being examined. In this analysis, it is assumed that the numerical final element strain energy is a predictor of spinal cord damage.

Unlike simulations of the effect of injuries to the spinal cord that have been done in the prior art, the present invention uniquely focuses on an analysis of stress applied to the central nervous system and not to the musculo-skeletal structures surrounding the central nervous system, except to the extent that such structures directly affect the central nervous system. None of the known prior art studies relating to vehicular injuries has analyzed the stresses on the central nervous system itself.

The present invention is believed to be the first method which is based on the assumptions set forth below, relating loads and stresses to spinal cord injury. These assumptions are:

i) Stretch and shear result in myelin and axonal injury;
ii) Common material properties can be assigned to areas of the spinal cord associated with common neurological function;
iii) It is possible to relate deformation and stresses to known neurological deficits in established clinical patient case histories; and
iv) One can develop a neurological damage database that predicts with reliability the mathematical probabilities of central nervous system injury.

In the methodology discussed above, it has been assumed that the spinal cord has uniform material properties (i.e. hardness, elasticity, etc.). That is, based on information obtained from clinical studies, it was assumed that the spinal cord has elastic properties that are heterogeneous across its entire cross-section. The method can be further refined by assigning different material properties to each of the various functional elements of the cord. In this more sophisticated model, the spinal cord can be considered as a deformable column of variable cross-section.

In the method described above, it was assumed that the diameter of each segment of the spinal cord is the same for all patients. To a first approximation, this is a reasonable assumption. However, there are variations in the diameter of the spinal cord among different patients, and sometimes this variation can be as much as about 50%. The model can be still further refined to take these differences into account. The initial measurement taken of the patient could include a measurement not only of the location of the spinal cord at each vertebral level, but also the diameter of the spinal cord at each such location. The latter information could then be incorporated into the model by making the two-dimensional graph correspond in size to the measured size, or approximate measured size, of the spinal cord of the patient being examined.

It should be appreciated that the major feature of the present invention is the construction of a meaningful finite-element model of the spinal cord, and the comparison of such model with comparable data obtained from previous patients. The greater the number of patients represented in a database, the more useful the present invention can be. The present invention therefore comprises, in part, a heuristic computer program that can learn from data observed in the past, to make predictions and/or inferences concerning the state of a given patient.

Finite element analysis, such as is applied in the above method, is commonly used in engineering problems. As stated earlier, the finite element model used in the present invention can be developed with the aid of the computer program called PRIME, which is especially suited for construction of finite element models. The PRIME program works well in implementing the present invention because it is designed to handle nodes, curves, lines, regions, and elements, all of which can be used to build up the model as described above. However, the invention is not limited to the use of any particular program. The method can be practiced with other software that facilitates the construction and manipulation of finite element models. Alternatively, new software for the same purpose could be written, by a person skilled in the art, based on the information given in this specification.

Figure 10:
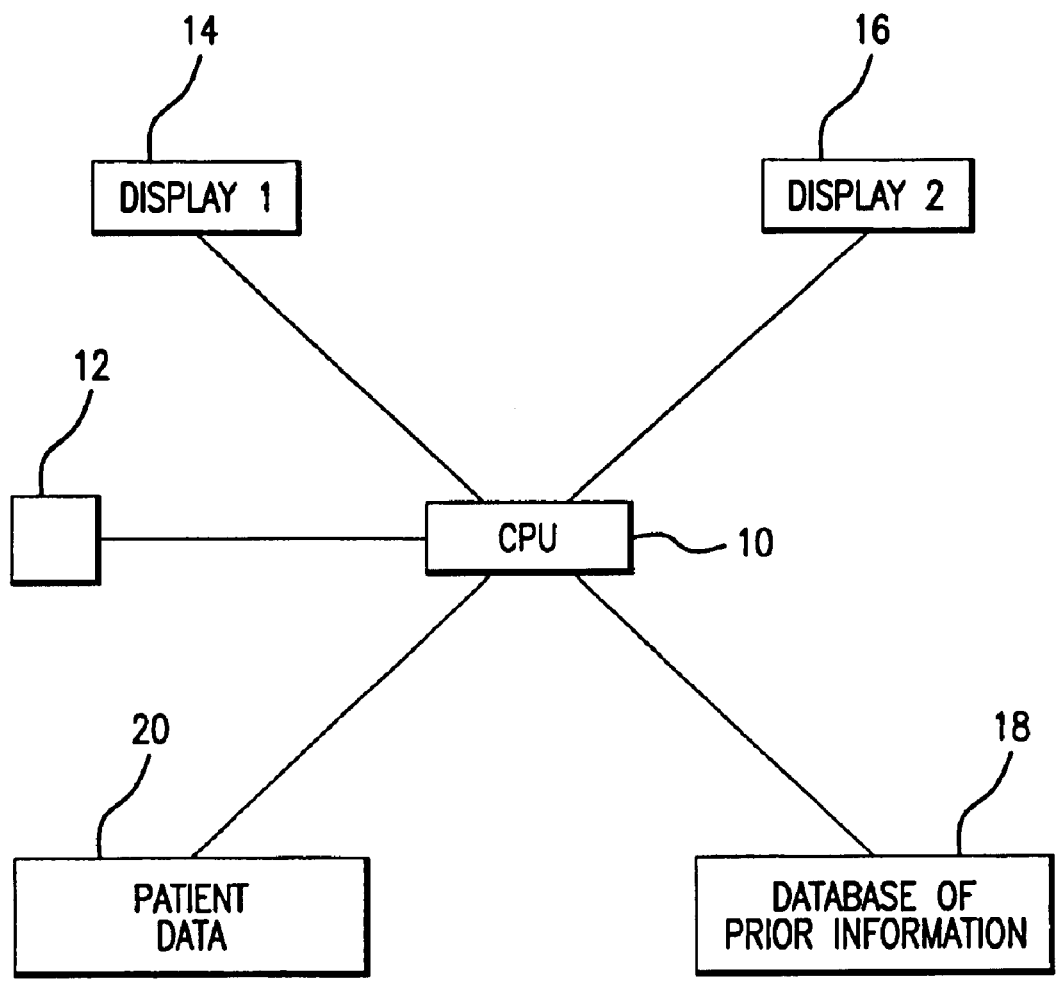
FIG. 10 provides a block diagram of an apparatus constructed according to the present invention.

An apparatus for implementation of the method described above is shown in the block diagram of FIG. 10. In one embodiment, the apparatus includes a central processing unit (CPU) 10 connected to display devices 14 and 16. A locating device 12, which could be a mouse or light pen, or equivalent, is connected to the CPU so that it can be used to select specific points on an image created by the displays. A database 18 is connected to the CPU, the database containing information on the spinal conditions of prior patients. The database could comprise a CDROM containing the data, or it could be provided in another form. The data in this database could include original patient data, models of the spinal cord of the patient derived from the original data, as well as information about the nature of the spinal injury observed in the patient, and other information. The CPU could be part of a personal computer, or a larger computer, or its equivalent.

The apparatus accepts, as input, the data containing the measurements taken as described above, for the patient of interest. These data, represented in block 20, may also be stored on a CDROM, or in any equivalent means that allows the data to be used by the CPU. As noted above, the patient data could be obtained by X-rays, by CT scanning, by magnetic resonance imaging (MRI), or by any means which enables the user to locate and digitize images of the spinal cord of the patient, at various vertebral levels, and for different positions assumed by the patient.

The data stored in block 20 are formatted by the CPU for display on display device 14. The user therefore sees, on display device 14, an image of the spinal cord of the patient, or multiple images of the spinal cord in various positions. Using the locating device 12, the operator then selects one or more points on the image(s) shown on the display. There is no fixed requirement concerning the number of data points that should be selected, but, in general, the larger the number of points, the more precise the resulting model.

When the operator indicates, to the system, that the operator is finished selecting data points, the system proceeds to construct a model of the spinal cord, using the method described earlier. The CPU includes a memory in which there is stored a representation of cross-sectional structures of the spinal cord, at the locations of various vertebrae, as is illustrated in FIGS. 2A and 2B. The CPU uses these stored representations, as described earlier, to construct one or more models of the spinal cord that are based on the actual data pertaining to the patient. The model so generated can be displayed on display device 16.

After completion of the model as described above, the operator may further specify appropriate constraints, and select biophysical material properties from a database of spinal properties. The operator may also specify hypothetical physical loading conditions. Any or all of the latter information is then used to calculate three-dimensional spinal tissue deformation, stresses, and strain energy resulting from the specified geometry, constraints, material properties, and physical loading. The results of this part of the process can then be superimposed on the display shown by display device 14. Thus, the device 14 can show both the original image of the spinal cord of the patient, and the predicted locations of maximum deformations and stress.

After performing the above steps, the system can provide a prediction of spinal damage, by comparing the digital model of the spinal cord of the patient, with the database represented by block 18. The database in block 18 preferably includes information on geometries, loading conditions, deformations, stress resultants, strain energy resultants, and known clinical damage results. The results of the comparison may be presented as a three-dimensional digital probability damage map, which can be superimposed onto the original image that was displayed by device 14. Preferably, the images shown on the display devices can be rotated and viewed in three-dimensional space, using commercially available software.

At the end of the process, the operator is given the opportunity to add the results of the digital model of the spinal cord, constructed for the patient under examination, to the database of block 18. The information added to the database therefore increases the internal "knowledge" of the system, and can enhance the utility of the system in making predictions in future cases. The more information in the database, the greater the ability of the system to make such predictions.

Although two separate display devices 14 and 16 are shown, the invention could be practiced with a single display device, using appropriate software to superimpose images, or to display them on split-screens, or to manipulate the images in other ways.

The finite element modeling used in the present invention should not be considered to be limited to acute spinal cord or brain injury. It is also applicable to chronic nervous system pathology, such as cervical stenosis, and possibly conditions such as syringomyelia, causalgia and temperomandibular joint syndrome wherein the geometric aspects and considerations similarly facilitate the use of the above-described methods.

The invention can be further modified, as will be apparent to the reader skilled in the art. Such modifications should be considered within the spirit and scope of the following claims.

What is claimed is:

1. A method of making a mathematical model of a spinal cord, comprising:
    a) measuring positions of a spinal cord at a plurality of vertebral levels of a patient, each measurement comprising the step of deriving a single point corresponding to each vertebral level,
    b) constructing and storing a plurality of two-dimensional graphs representing cross-sections of a human spinal cord at locations corresponding to said plurality of vertebral levels, wherein said two-dimensional graphs are independent of any measurement performed on the patient, and
    c) stacking said plurality of two-dimensional graphs so as to produce a three-dimensional model of at least a portion of the spinal cord, wherein each two-dimensional graph is placed in a location corresponding to the corresponding position measured in step (a).

2. The method of claim 1, further comprising causing the patient to assume each of a plurality of positions, wherein the measuring step is performed for each of said plurality of positions, and wherein steps (a) through (c) are performed for each of said plurality of positions.

3. The method of claim 2, further comprising comparing the three-dimensional models of the spinal cord to data stored in a database, the database containing similar data obtained from other patients.

4. The method of claim 1, further comprising comparing the three-dimensional model of the spinal cord to data stored in a database, the database containing similar data obtained from other patients.

5. The method of claim 1, wherein step (b) includes the step of simulating a stress applied to at least one portion of the spinal cord, wherein the three-dimensional model represents at least a portion of the spinal cord in a perturbed condition.

6. The method of claim 5, further comprising comparing the three-dimensional models of the spinal cord to data stored in a database, the database containing similar data obtained from other patients.

7. The method of claim 1, wherein the two-dimensional graphs are produced by dividing cross-sections of the spinal cord into a plurality of finite elements, wherein the three-dimensional model produced in step (c) is formed of a plurality of finite elements.

8. A method of making a mathematical model of at least a portion of a spinal cord, comprising:
    a) measuring positions of a spinal cord at a plurality of vertebral levels of a patient, each measurement comprising the step of deriving a single point corresponding to each vertebral level,
    b) constructing and storing a plurality of two-dimensional graphs representing cross-sections of a human spinal cord at a plurality of vertical locations, wherein said two-dimensional graphs are independent of any measurement performed on the patient, the two-dimensional graphs being assembled from a plurality of finite elements, the finite elements being coded according to a neurological function of a region of the spinal cord in which said element is located, and c) stacking said plurality of two-dimensional graphs according to the positions of the spinal cord measured in step (a) so as to produce a three-dimensional model of at least a portion of the spinal cord, wherein each two-dimensional graph is placed in a location corresponding to the corresponding position measured in step (a), wherein said three-dimensional model is made of a plurality of finite elements.

9. The method of claim 8, further comprising repeating steps (a) through (c) for each of a plurality of positions assumed by the patient.

10. The method of claim 9, further comprising comparing the three-dimensional model with data collected in a similar manner from other patients.

11. The method of claim 8, further comprising comparing the three-dimensional model with data collected in a similar manner from other patients.

12. The method of claim 8, wherein step (b) also comprises simulating a stress applied to at least a portion of the spinal cord, wherein the two-dimensional graphs and the three-dimensional model represent the spinal cord in a perturbed condition.

13. The method of claim 12, further comprising comparing the three-dimensional model with data collected in a similar manner from other patients.

14. Apparatus for making a mathematical model of a spinal cord, comprising:

a) means for measuring positions of a spinal cord at a plurality of vertebral levels of a patient, wherein the measuring means comprises means for deriving a single point corresponding to each vertebral level, b) means for constructing and storing a plurality of two-dimensional graphs representing cross-sections of a human spinal cord at a plurality of vertical locations, wherein said two-dimensional graphs are independent of any measurement performed on the patient, and c) means for stacking said plurality of two-dimensional graphs according to measured positions determined by the measuring means, so as to produce a three-dimensional model of at least a portion of the spinal cord.

15. The apparatus of claim 14, further comprising means for comparing the three-dimensional model of the spinal cord to data stored in a database, the database containing similar data obtained from other patients.

16. The apparatus of claim 14, further comprising means for simulating a stress applied to at least one portion of the spinal cord, wherein the three-dimensional model represents at least a portion of the spinal cord in a perturbed condition.

17. The apparatus of claim 16, further comprising means for comparing the three-dimensional models of the spinal cord to data stored in a database, the database containing similar data obtained from other patients.

18. The apparatus of claim 14, wherein the constructing means comprises means for dividing cross-sections of the spinal cord into a plurality of finite elements, wherein the three-dimensional model is formed of a plurality of finite elements.

19. Apparatus for making a mathematical model of at least a portion of a spinal cord, comprising:

a) means for measuring positions of a spinal cord at a plurality of vertebral levels of a patient, wherein the measuring means comprises means for deriving a single point corresponding to each vertebral level, b) means for constructing and storing a plurality of two-dimensional graphs representing cross-sections of a human spinal cord at a plurality of vertical locations, wherein said two-dimensional graphs are independent of any measurement performed on the patient, the two-dimensional graphs being assembled from a plurality of finite elements, the finite elements being coded according to a neurological function of a region of the spinal cord in which said element is located, and c) means for stacking said plurality of two-dimensional graphs according to the positions of the spinal cord at said vertebral levels measured by the measuring means, so as to produce a three-dimensional model of at least a portion of the spinal cord, wherein said three-dimensional model is made of a plurality of finite elements.

20. The apparatus of claim 19, further comprising means for comparing the three-dimensional model with data collected in a similar manner from other patients.

21. The apparatus of claim 19, wherein the constructing means includes means for simulating a stress applied to at least a portion of the spinal cord, wherein the two-dimensional graphs and the three-dimesional model represent the spinal cord in a perturbed condition.

22. The apparatus of claim 21, further comprising means for comparing the three-dimensional model with data collected in a similar manner from other patients.

* * * * *